(12) United States Patent
Krishnan

(10) Patent No.: US 6,682,565 B1
(45) Date of Patent: Jan. 27, 2004

(54) JOINT PROSTHESIS

(75) Inventor: Jeganath Krishnan, Unley Park (AU)

(73) Assignee: Flinders University, South Australia (AU)

( * ) Notice: Subject to any disclaimer, the term of this patent is extended or adjusted under 35 U.S.C. 154(b) by 4 days.

(21) Appl. No.: 10/088,317

(22) PCT Filed: Sep. 14, 2000

(86) PCT No.: PCT/AU00/01097

§ 371 (c)(1),
(2), (4) Date: Jul. 18, 2002

(87) PCT Pub. No.: WO01/19294

PCT Pub. Date: Mar. 22, 2001

(30) Foreign Application Priority Data

Sep. 14, 1999 (AU) ............................................. PQ2820

(51) Int. Cl.⁷ .................................................. A61F 2/42
(52) U.S. Cl. .................................................... 623/21.16
(58) Field of Search .......................... 623/21.16, 21.17, 623/21.11, 21.19, 21.15, 21.13

(56) References Cited

U.S. PATENT DOCUMENTS

| | | | |
|---|---|---|---|
| 3,946,445 A | | 3/1976 | Bentley et al. |
| 4,242,759 A | | 1/1981 | White |
| 4,304,011 A | | 12/1981 | Whelan, III |
| 5,674,297 A | * | 10/1997 | Lane et al. ............... 623/21.16 |
| 5,782,927 A | | 7/1998 | Klawitter et al. |
| 5,938,700 A | * | 8/1999 | Lippincott, III .......... 623/21.15 |
| 6,383,223 B1 | * | 5/2002 | Baehler et al. .......... 623/21.11 |
| 6,423,097 B2 | * | 7/2002 | Rauscher ................. 623/21.16 |

FOREIGN PATENT DOCUMENTS

EP  0 289 276 A1  11/1988

* cited by examiner

Primary Examiner—Pedro Philogene
Assistant Examiner—David A Bonderer
(74) Attorney, Agent, or Firm—M. Lisa Wilson; Hale and Dorr LLP

(57) ABSTRACT

A prosthesis (2) for replacing a joint between first and second articulating bones (10, 12), the prosthesis comprising first and second joint members (4, 6) and wherein: the first joint member includes a first mounting member (26) which in use is mounted in an intramedullary canal (22) of the first bone; the second joint member includes a second mounting member (28) which in use is mounted in an intramedullary canal (27) of the second bone; the first joint member has a ball (30) having a first part spherical surface and a slot (34) extending transversely through the ball; the second joint member has a socket (52) having a second part spherical surface which is complementary to first spherical surface and a guide peg (60) which projects from the second spherical surface and in use is located in said slot; and wherein the guide peg is loose fit within the slot thereby permitting biaxial rotation of the second member relative to the first member about at least first and second axes (14, 16).

33 Claims, 14 Drawing Sheets

JOINT PROSTHESIS

This invention relates to a joint prosthesis.

More particularly, the invention relates to a prosthesis which can be used to replace a metacarpo phalangeal joint although the principles of the invention are applicable to prostheses for other joints where there is some degree of biaxial rotation required.

The metacarpo phalangeal joint prosthesis is employed by surgeons to help patients with arthritis affecting an MCP joint. The aim of the prosthesis is to correct deformity, relieve pain, improve the range of movement of the joint, maintain stability, and therefore improve hand function. Known MCP joint prosthesis include single piece silastic products known as the Swanson and Sutter joints. In these products, the essential pivotal action is provided by an integral web hinge between the metacarpal and phalangeal components of the prosthesis. These components include integral intramedullary stems which are not fixed in place but are slidably retained in the respective bone cavities. The stems are rectangular to prevent rotation and are designed to piston within the cavity. The products rely to an extent on the development of scar tissue to encapsulate the joint.

Prosthesis of this type have been successful in achieving pain relief. The arc of motion achieved, around 40° to 60°, is sufficient to improve hand function relative to pre-insertion arthritic conditions. On the other hand, it is considered by many that the prosthesis does not provide adequate stability for the joint and there is a significant incidence of fracture at the hinge and/or stems, and of dislocation. The latter occurs when the stems slide out of the bone cavities after significant wear. There has also been an increasing longer term association with silicon synovitis, and with disintegration of the prosthesis.

An adaptation of the integral hinge prosthesis was the Niebauer prosthesis in which the stems were surrounded by fibre mesh so that intramedullary fixation could be obtained by fibrous growth into the mesh. Clinical review demonstrated that flexion at the hinge did not occur due to soft tissue interposition, and that there was a tendency for fracture at the hinge and at the distal stem. The Helat MCP flap joint had a dorsal ulnar based flap to maintain central position with respect to the extensor tendon.

In general, integral hinge prostheses have been characterised, relative to earlier highly constrained linked structures, by increased restriction of movement imposed by the design of the prosthesis, but by a corresponding increased reliance on soft tissues around the joint to provide stability, maintain alignment and correction of deformity. Problems met have included implant failure due to material failure or fracture at the hinge or stem, inadequate range of movement due to soft tissue interposition at the hinge, and inadequate rigidity of the implant leading to recurrence of ulnar deviation deformity.

In an attempt to reduce the stresses on the implant, and to better stimulate the normal anatomy of the articulating surfaces at the MCP joint, unrestrained implants have been proposed. An example was the WEL MCP joint disclosed in U.S. Pat. No. 4,242,759 in which the metacarpo and phalangeal components are not connected together. In the second embodiment described in that patent, the phalangeal component has a transverse ridge which traverses a complementary trough or groove in the metacarpo component. The different lateral articulation of the joint at the extended and clench positions is simulated by providing a close fit between the ridge and groove at one position and a fit with lateral articulating freedom at another position. A published paper concluded that this jointed tended to dislocate as it was too reliant on the stability of surrounding tissue, a condition which cannot be met in cases of rheumatoid arthritis. A further proposal in this category in the Stokoe-Unsworth prosthesis, described in PhD thesis by Stokoe, which is still at a developmental stage. This prosthesis is an unconstrained surfacing implant with a spherical contoured metacarpo component and a corresponding saucer-shaped phalangeal component.

U.S. Pat. No. 3,946,445 discloses a structure somewhat similar to that of U.S. Pat. No. 4,242,759 save that the rib and an associated pair of grooves are on the metacarpo component. Like the other patent, this reference shows mounting of the components by respective tapered solid intramedullary stems.

U.S. Pat. No. 5,938,700 is another example of a metacarpo phalangeal joint. In this prosthesis, a ball and socket type of connection is provided, the ball being provided with a dovetail rib which is received within a dovetail slot formed on respective members. This is an example of a restrained implant and, because of the interlocking-dovetails, is essentially incapable of providing for any ulnar or radial deviation.

These unconstrained prostheses were designed in an attempt to reduce the stresses on the implant and at the site of fixation, and to recreate the normal anatomy of the articulating surfaces at the MCP joint. The success of these implants depends on early surgery, and on good soft tissue reconstruction. They are highly reliant on the soft tissue surrounding the joint for joint stability and the prevention of deformity recurrence. The difficulty with these premises is that early surgery is rarely needed or attempted since, at that stage, the patients have good hand function and surgery is generally not therefore indicated. Moreover, in the rheumatoid process where soft tissue is inflamed and where there is a tendency for soft tissue deformation to occur, it is unlikely that unrestrained prosthesis will stand the test of time.

The current practical situation, therefore, is that MCP prostheses are typically only recommended in extreme cases. Surgeons generally do not regard presently available products as entirely satisfactory. The technology is relatively crude and unsatisfactory in comparison to knee and hip joints, which have reached a high level of reliability and are therefore commonly inserted. There is a need for an MCP prosthesis that allows the joint a functional range of movement in most of the normal planes of joint motion while at the same time incorporating some constraint to limit soft tissue deformity and to provide stability. It is an object of the invention to at least in part meet this objective.

According to the present invention there is provided a prosthesis for replacing a joint between first and second articulating bones the prosthesis comprising first and second joint members and wherein:

the first joint member includes a first mounting member which in use is mounted in an intramedullary canal of the first bone;

the second joint member includes a second mounting member which in use is mounted in an intramedullary canal of the second bone;

the first joint member has a ball having a first part spherical surface and a slot extending transversely through the ball;

the second joint member has a socket having a second part spherical surface which is complementary to first spherical surface and a guide peg which projects from the second spherical surface and in use is located in said slot; and wherein the guide peg is loose fit within the slot thereby permitting biaxial rotation of the second member relative to the first member about at least first and second axes.

The invention also provides a prosthesis for replacing a joint between first and second articulating bones the prosthesis comprising first and second joint members and wherein:

the first joint member includes a first mounting member which in use is mounted in an intramedullary canal of the first bone;

the second joint member includes a second mounting member which in use is mounted in an intramedullary canal of the second bone;

the first joint member has a ball having a first part spherical surface and a slot extending transversely through the ball;

the second joint member has a socket having a second part spherical surface which is complementary first spherical surface and a guide peg which projects from the second spherical surface and in use is located in said slot; and wherein the socket is encircled by an annular lip.

The invention also provides a method of providing a prosthesis for a joint between first and second articulating bones using a prosthesis as defined above including the steps of removing adjacent parts of the first and second bones to expose first and second intramedullary canals and fixing the first and second mounting members in the first and second intramedullary canals, respectively.

In the preferred form of the invention, the first and second bones are metacarpal and phalangeal bones, respectively.

Preferably further, the method enables the prosthesis to provide up to about 90° of flexion, 10° of extension, 25° radial deviation and/or 5° ulnar deviation and a small degree of axial rotation, i.e. pronation and/or supination.

The invention will now be further described with reference to the accompanying drawings, in which.

Figure 1:
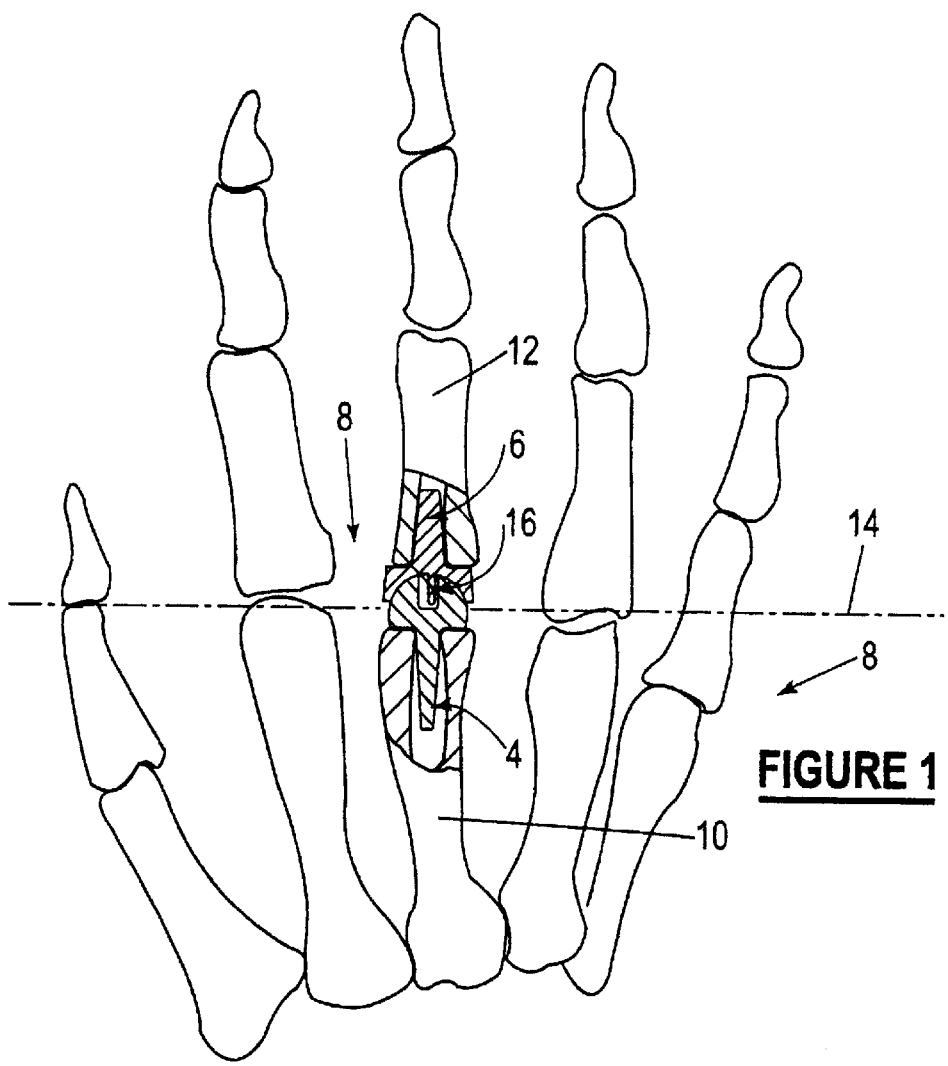
FIG. 1 is a schematic view of the bones of a right hand showing a prosthesis of the invention mounted therein.

The drawings show a prosthesis 2 of the invention which is constructed for use as a metacarpo phalangeal joint. The prosthesis comprises a ball component 4 which in use is connected to one of the metacarpal bones of a patient and a socket component 6 which in use is connected to one of the phalangeal bones of a patient. FIG. 1 schematically illustrates the use of the prosthesis 2 as a replacement joint in the right hand of a patient. FIG. 1 shows the bones of the hand from the dorsal side, i.e. with the palm down. The ball component 4 is mounted in one of the metacarpal bones 10 and the socket component 6 is mounted in the adjacent phalangeal bone 12. The prosthesis 4 permits rotation of the bone 12 relative to the bone 10 about a generally horizontal axis 14 and about a generally vertical axis 16, as will be described in more detail below.

Figure 1A:
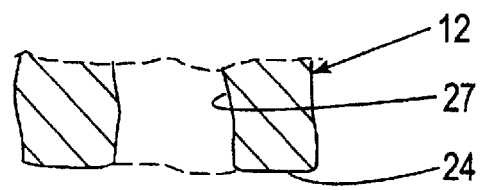
FIG. 1A is an enlarged schematic view of some of the bones.
Figure 1A:
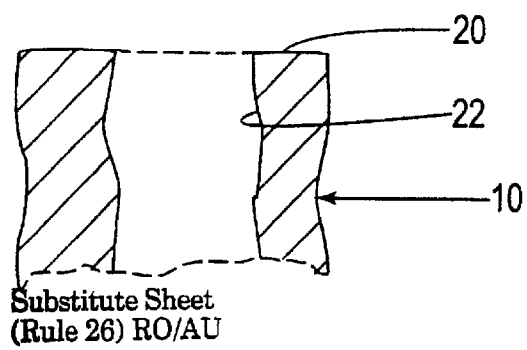

The prosthesis of the invention is normally used where the natural joint of a patient has deteriorated through rheumatoid arthritis. The surgeon removes the end of the metacarpal bone 10 so as to form a generally annular metacarpal end face 16 and to expose the metacarpal intramedullary canal 22 as shown in FIG. 1A. The surgeon also removes the end of the adjacent phalangeal bone 12 so as to form a generally annular phalangeal end face 24 and expose the intramedullary canal 27 of the phalangeal bone 12, as also diagrammatically shown in FIG. 1A. The ball component 4 includes a mounting stem 26 which is inserted into the canal 22. Similarly, the socket component 6 includes a mounting stem 28 which is inserted into the canal 27, as will be described in more detail below. The surgeon preferably leaves the tubercle of both bones so as not to significantly disturb attachment sites for the collateral ligaments. Preferably stems 26 and 28 are cemented in the canals 22 and 27 using a known bone cement.

A patient may require from one to four replacement joints in each hand. The prostheses needs to be made in a number of convenient sizes so as to suit the anatomical requirements of patients. Further, mirror images of the socket component 6 need to be provided for use in the left hand. The ball components 4 are the same for the right and left hands.

Figure 2:
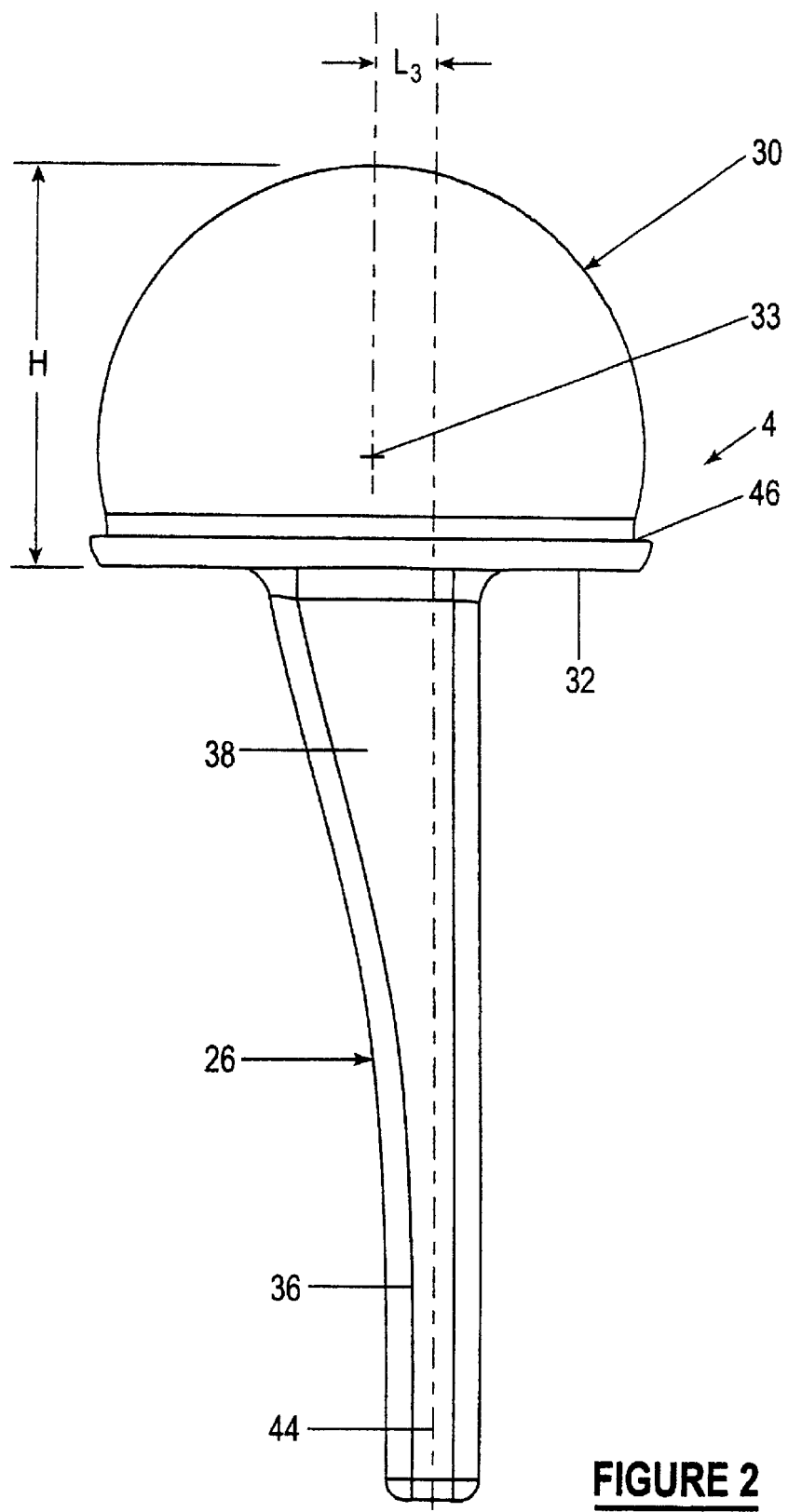
FIG. 2 is a side view of the ball component of the prosthesis with the dorsal side on the right.
Figure 3:
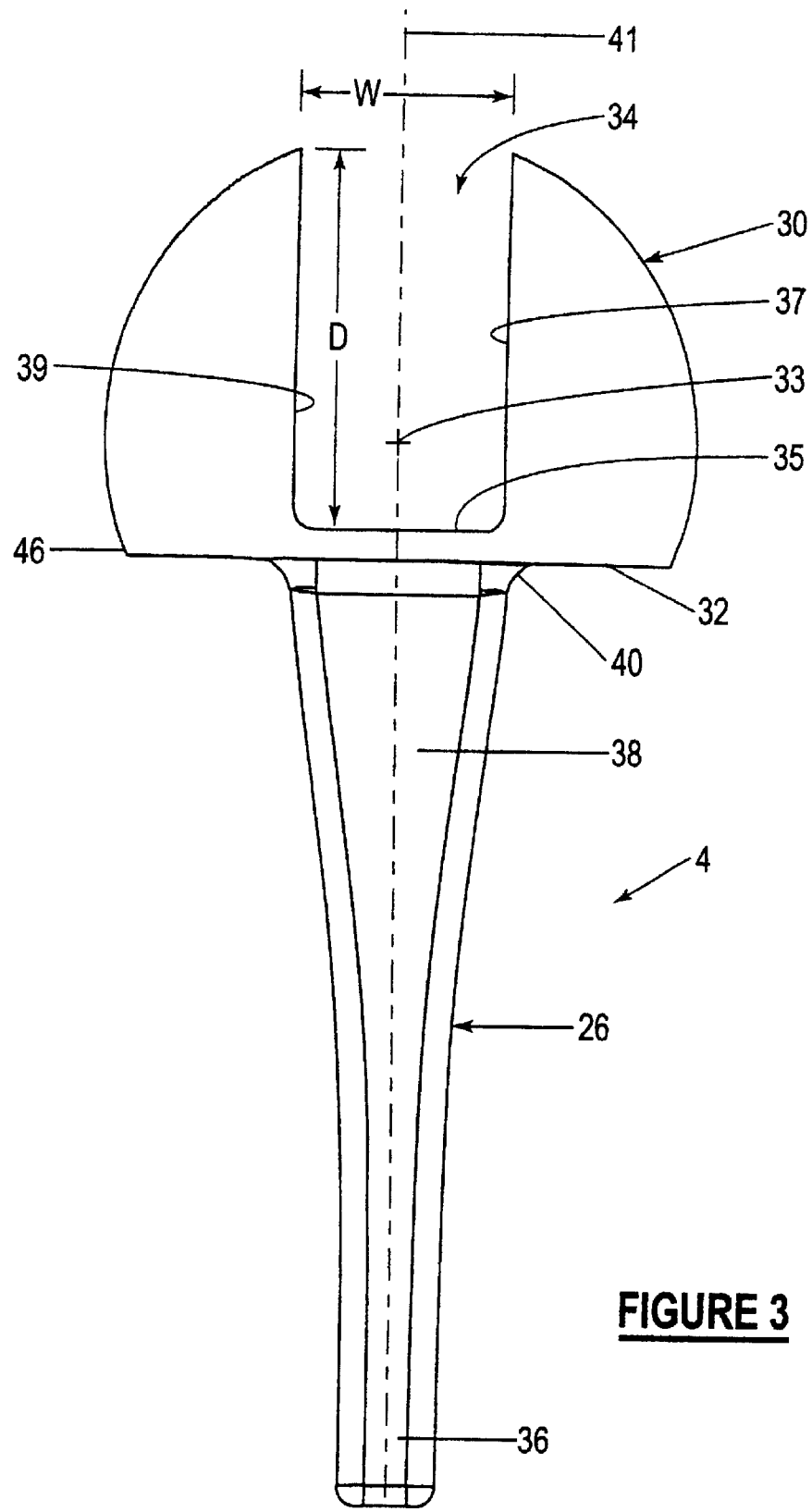
FIG. 3 is a plan view of the ball component as viewed from the dorsal side.
Figure 4:
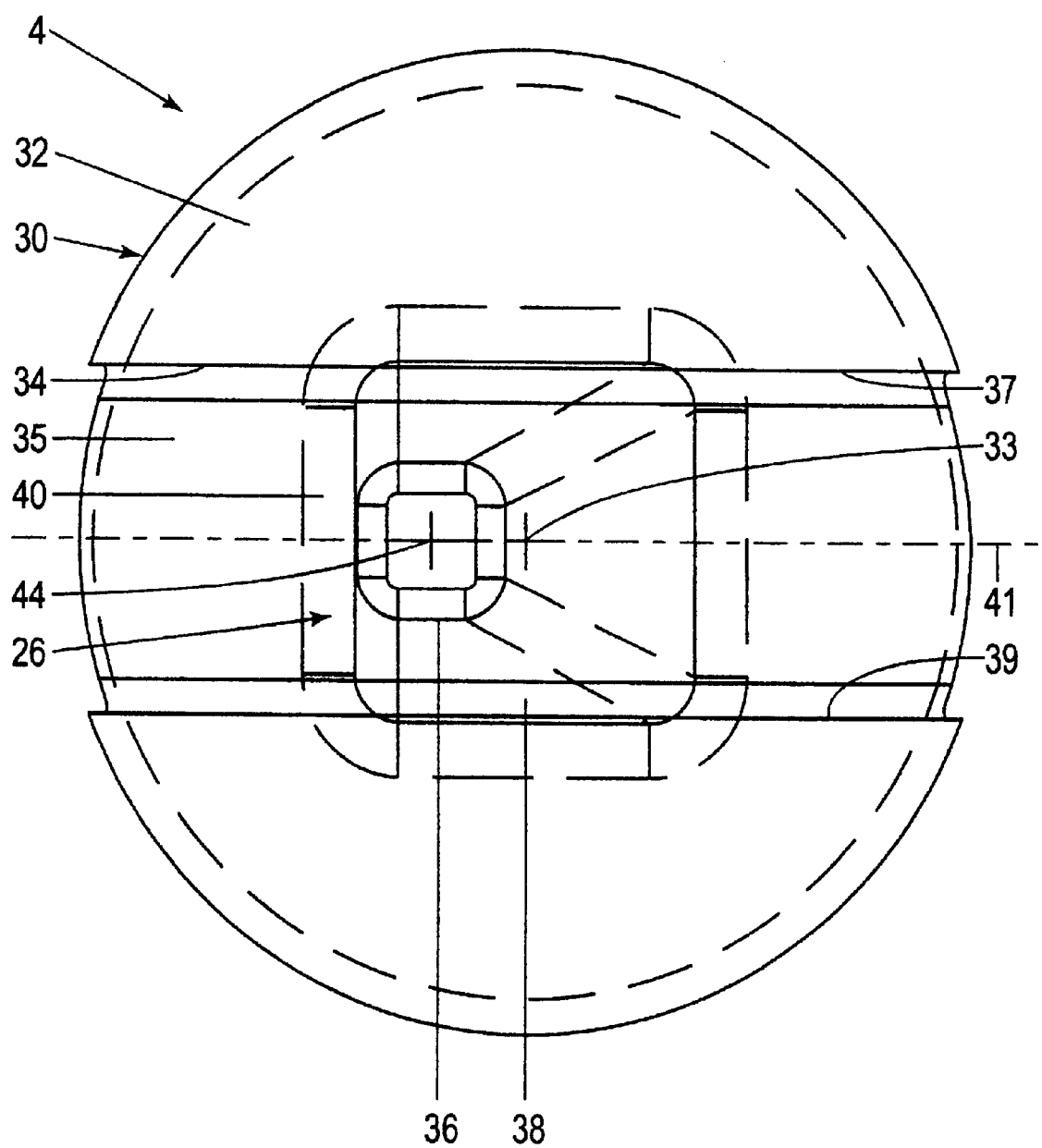
FIG. 4 is an end view of the ball component.

FIGS. 2, 3 and 4 illustrate the ball component in more detail. It will be seen that the ball component 4 includes a ball 30 having a part spherical surface having a centre 33. The ball 30 has a flat base 32 from which the mounting stem 26 projects. The ball 30 includes a wide slot 34 extending through the ball 30, the slot 34 being open at both ends to the surface of the ball 30. The slot 34 extends diametrically through the ball 30. It is defined by a base 35 and parallel sidewalls 37 and 39 which are perpendicular to the base 35 and joined thereto by rounded corners. The base 35 of the slot is parallel to the flat base 32. The slot 34 has a central plane 41 which is parallel the sidewalls 37 and 39 and includes the centre 33. The ball component 4 is symmetrical about the central plane 41.

As seen in FIG. 3, the stem 26 has a narrow proximal end 36 and a wider distal end 38. The tapering is chosen so as to generally conform to the typical dimensions of the metacarpal canal 22. As seen in FIG. 4, the stem 26 is generally rectangular in cross-section but having rounded corners so as to facilitate insertion and avoid stress points in the bone. The distal end 38 merges into the base surface 32 by radiussed portions 40 so as again to avoid stress points. The proximal end 36 has a centreline 44 which, as seen in plan view in FIGS. 3 and 4 extends through the central plane 41 of the component 4 and the slot 34, as seen in plan in FIG. 3. As shown in FIG. 2, it will be seen that the centreline 44 is offset relative to the centre of the distal end 38 of the stem 26 and the centre 33 of the ball 30. The centre 33 of the spherical surface is offset by a distance $L_3$ relative to the centreline 44. This results in the centreline 44 being offset dorsally with respect to the centre of the base plate 32. This geometry allows for better simulation of normal metacarpal kinematics. The magnitude of the offset $L_3$ will depend upon the size of the component. Typically the distance $L_3$ is in the range 0.18 $R_1$ to 0.26 $R_1$, where $R_1$ is the radius of the surface of the ball 30.

The length of ball H, which is the distance from the flat base 32 to the apex of the ball 30, is 1.4 $R_1$ as shown in FIG. 2.

The width W of the slot 34 also varies in accordance with the size of the joint It too can best be expressed in terms of its comparative size to the radius which forms the ball 30. Preferably, the width W of the slot 34 is in the range 0.67 $R_1$ to 0.75 $R_1$ and most preferably 0.71 $R_1$. The depth D of the slot 34, which is the distance from surface 35 to the apex of the ball 30 on axis 41, is preferably in the range 1.17 $R_1$ to 1.43 $R_1$ and most preferably 1.3 $R_1$.

Figure 8:
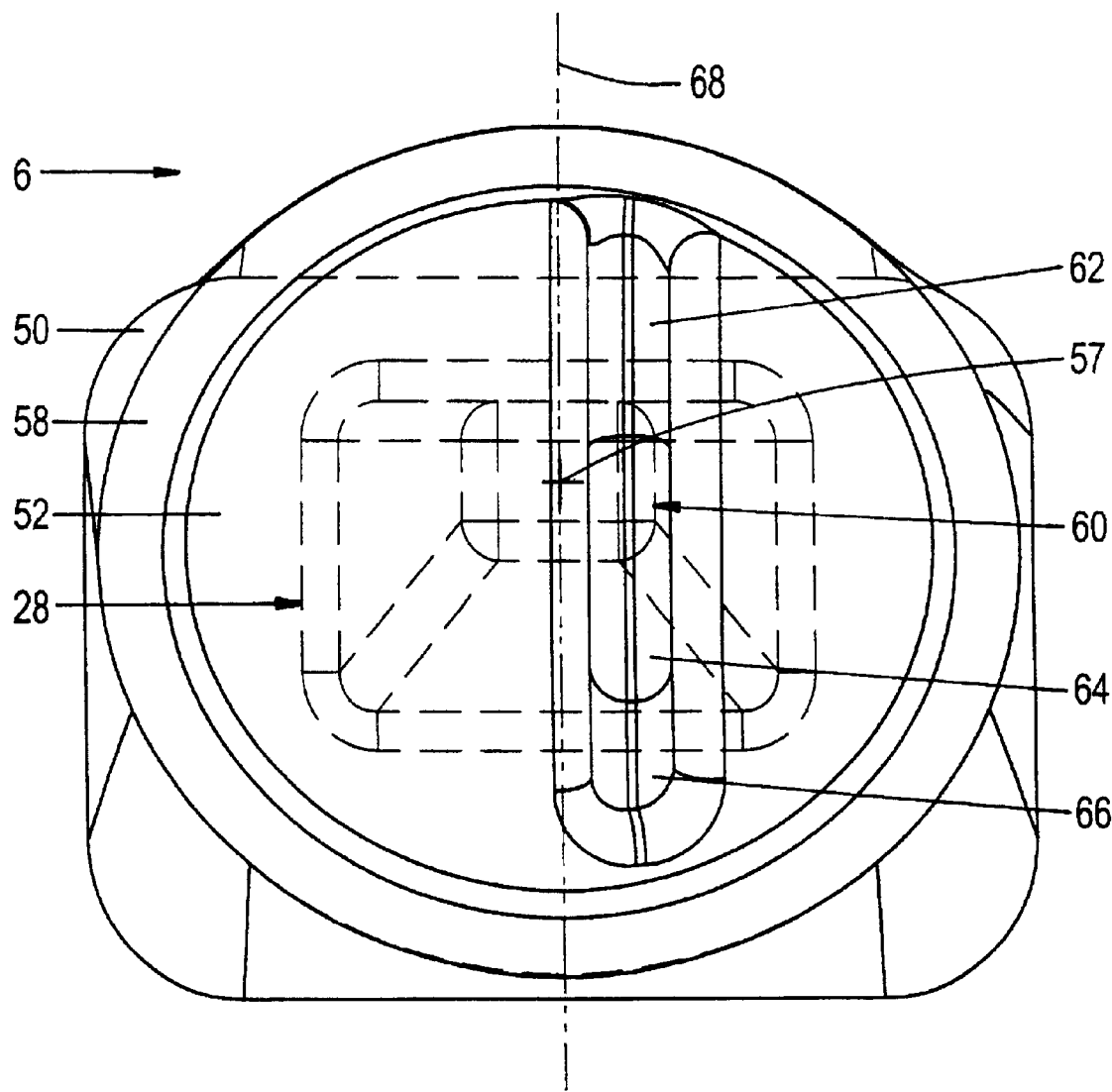
FIG. 8 is an end view of the socket component.

The socket component 6 is illustrated in more detail in FIGS. 5 to 8. The socket component includes a body portion 50 which includes a spherical bearing surface 52 which is complementary in shape to the spherical surface which forms the ball 30. The body 50 includes a base surface 54 from which the mounting stem 28 extends, the proximal end of the stem 28 merging into the base surface 54 by means of a radiussed portion 56. As best seen in FIG. 8, the stem 28 is generally rectangular in cross section but has rounded corners so as to again facilitate insertion into the phalangeal canal 27 and avoid stresses.

Figure 5:
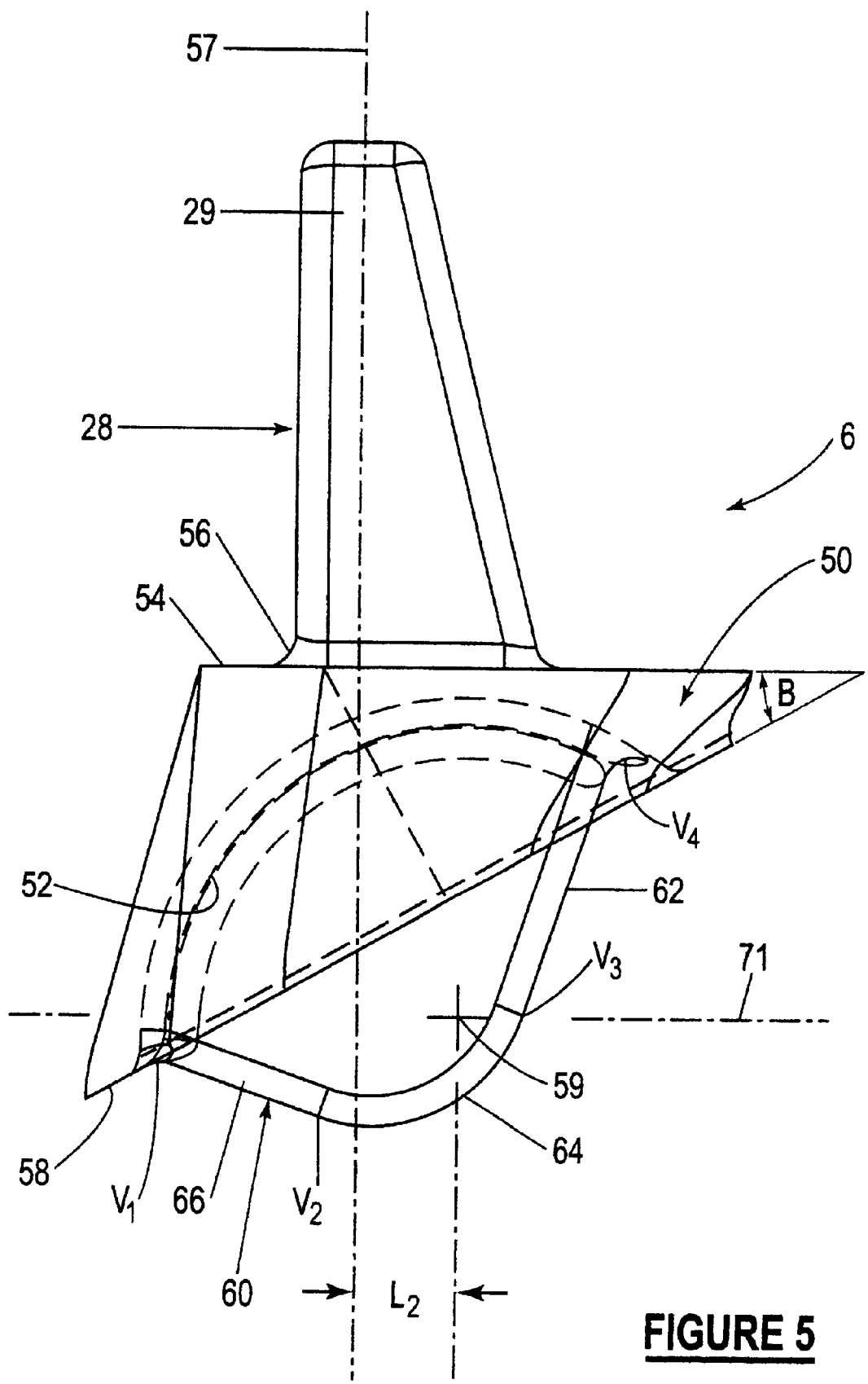
FIG. 5 is a side view of the socket component with the dorsal side on the left.
Figure 6:
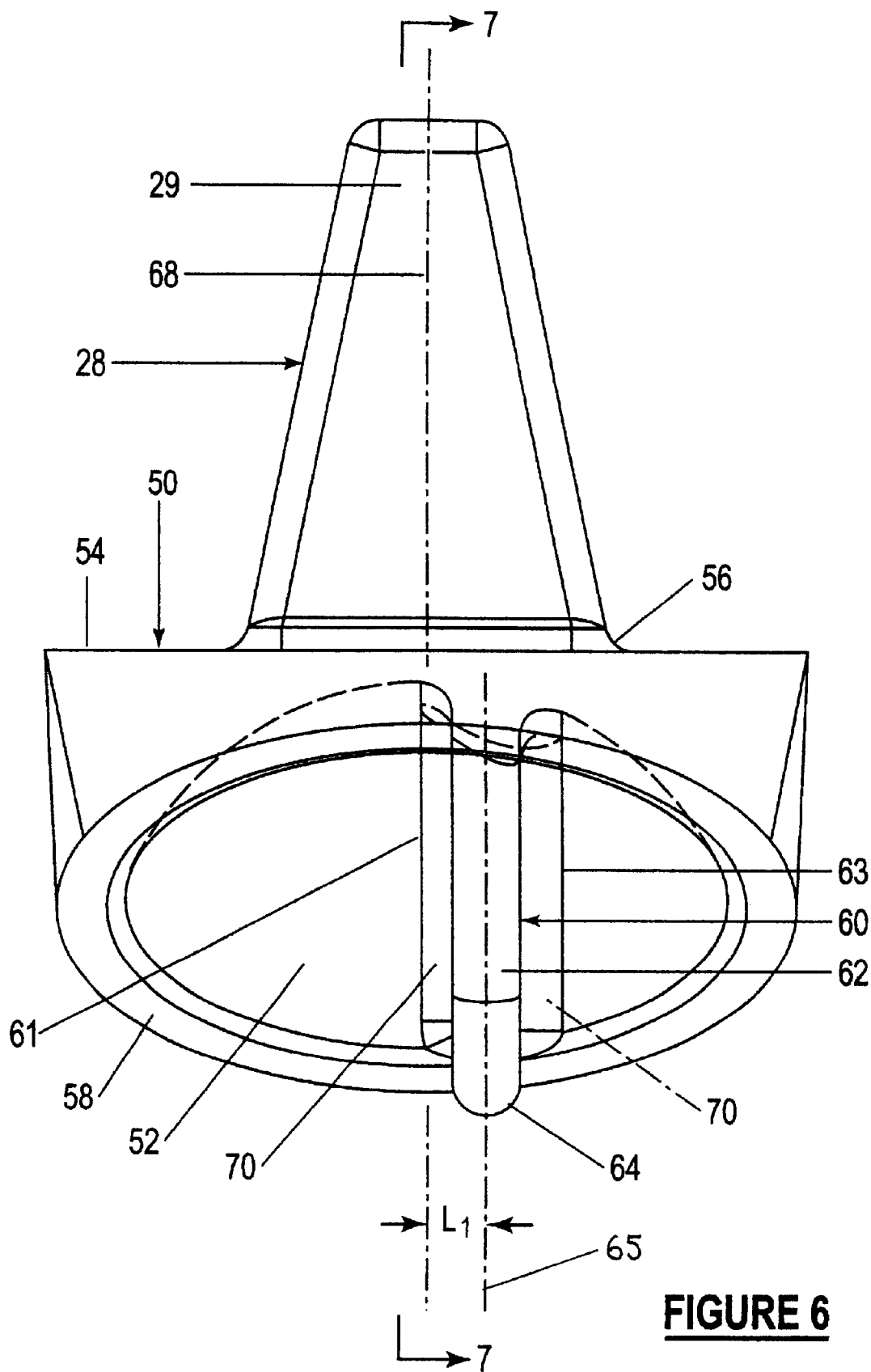
FIG. 6 is a plan view of the socket component.
Figure 7:
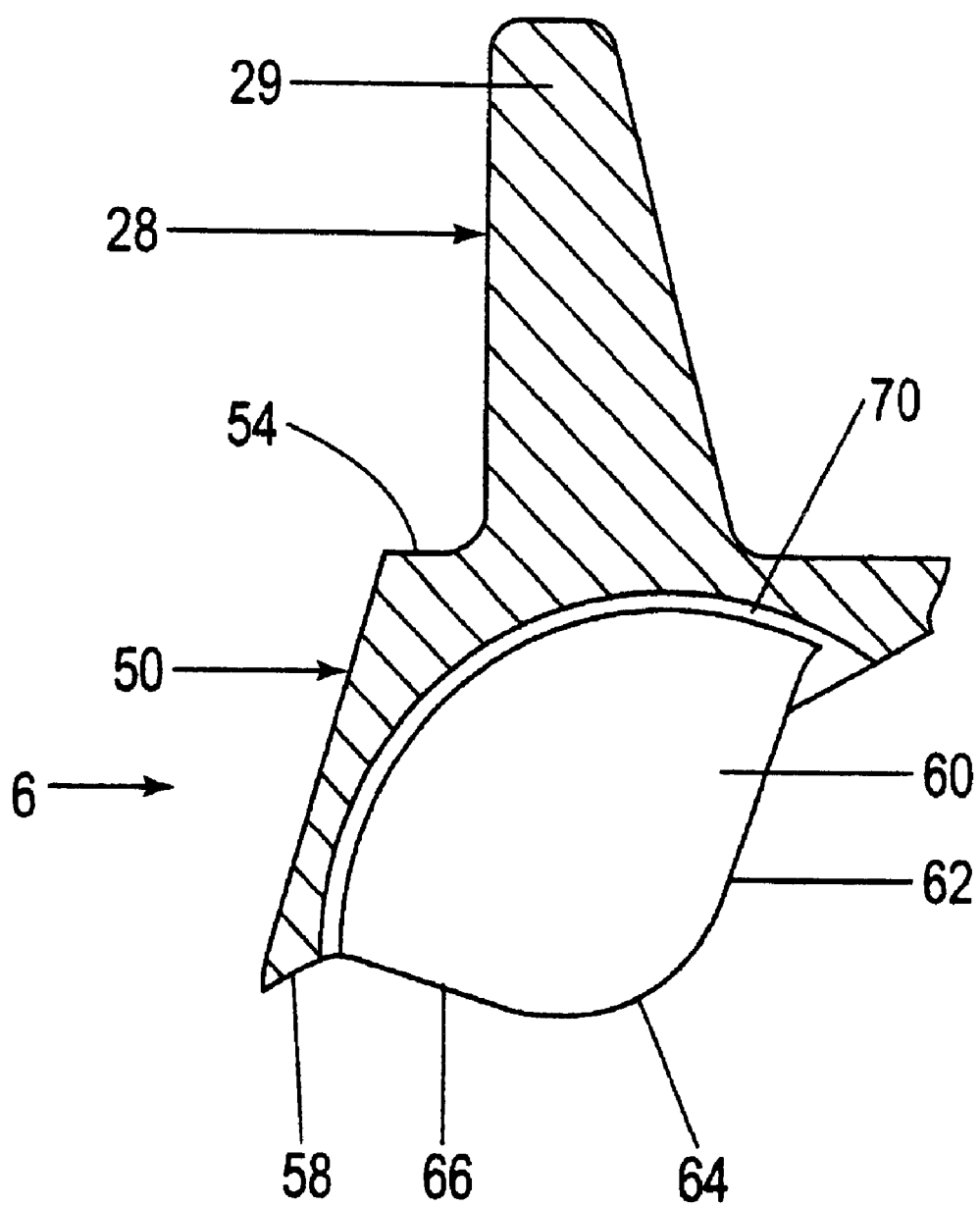
FIG. 7 is a sectional view along the lines 7—7.

As best seen in FIG. 6, the body 50 includes an annular lip 58 which extends generally around the periphery of the spherical bearing surface 52. The lip 58 lies in a plane which is disposed at an angle B relative to the plane of the base 54 as best seen in FIG. 5. Preferably the angle B is in the range 25° to 35° and most preferably 28°. The width of the lip 58 is in the range 0.09 $R_1$ to 0.11 $R_1$. Preferably the width is 0.1 $R_1$.

The spherical surface which forms the bearing surface 52 has a centre 59. As will be explained below, in the assembled joint, the centre 59 is coincident with the centre 33 of the ball 30. The centre 59 is offset by a distance $L_2$ relative to a centreline 57 which passes through the distal end of the stem 29, as shown in FIG. 5. The distance $L_2$ will depend on the size of the joint and it is best expressed as a function of the radius $R_1$. The offset $L_2$ is preferably about 0.36 $R_1$ to 0.44 $R_1$ and most preferably about 0.4 $R_1$.

Nominally the radius $R_2$ which defines the spherical bearing surface 52 is the same as the radius $R_1$ of the ball but preferably it is made about 0.5% larger so as to provide a small clearance (e.g. 0.0225 to 0.0413 mm) to allow fluid to enter the joint, providing lubrication and minimising wear.

As seen in plan view in FIG. 6, the stem 28 and body 50 include a central plane 68 about which the stem 28 and bearing surface 52 are symmetrical.

The body 50 is integrally formed with a guide peg 60 which projects outwardly from the spherical bearing surface 52 and extends beyond the lip 58, as shown in FIG. 5. The peg 60 has a central plane 65 which lies on a chord of the spherical surface 52 and the centre 57 is parallel to the plane 65. The peg 60 has parallel side faces 61 and 63 which are symmetrically disposed on either side of the central plane 65. The edge of the peg, as seen in side view, includes a first volar straight portion 62, curved central portion 64 and straight dorsal portion 66. The volar portion 62 is longer than the dorsal portion 66 so that the peg is somewhat skewed towards the dorsal side of the joint, as shown in FIG. 5. This geometry is necessary to allow the required flexion and extension to be achieved as well as provide stability during distraction of the joint surfaces. The peg can be described by vertices $V_1$, $V_2$, $V_3$ and $V_4$. $V_1$ and $V_2$ define the straight dorsal portion 66 while $V_3$ and $V_4$ define the straight volar portion 62. The vertices $V_1$ to $V_4$ are measured as vertical distances to a horizontal line 71 which passes through the centre 59. These vertices ($V_1$ to $V_4$) define the location of the straight portions with respect to the centre 59. The relationships are best expressed as a function of $R_2$ as follows:

$V_1 = 0.0305\ R_2$ $V_2 = 0.204\ R_2$ $V_3 = 0.0951\ R_2$ $V_4 = 0.903\ R_2$

These values can be varied by ±5%. The radius of the curved central portion 64 can best be expressed as a function of $R_2$ which is 0.4834 $R_2$.

As best seen in FIGS. 6 and 8, the peg 60 is offset relative to the central plane 68 by a distance $L_1$. Preferably the distance $L_1$ is in the range 0.163 $R_1$ to 0.181 $R_1$ and preferably 0.172 $R_1$. The orientation of the offset is in the ulnar direction, i.e. in the direction away from the thumb of the hand 8, i.e. to the right when looking in plan at the dorsal side of a right hand and to the left when looking in plan at the dorsal side of a left hand. It will be also seen that the edges 62, 64 and 66 are rounded (as seen in transverse section in FIG. 12) and also the base of the peg 60 merges into the surface 52 by radiussed portions 70. The thickness of the peg 60 is preferably in the range 0.19 to 0.21 times $R_1$ and most preferably 0.2 times $R_1$.

The components 4 and 6 are preferably manufactured from cobalt-chrome molybdenum alloy of known type. The components are preferably manufactured with a high degree of precision and are precision polished to be within high tolerances. The surfaces 30 and 52 are of critical importance to the functional life of the joint. Normally, these have a sphericity to a tolerance of about 0.005 mm and a surface finish to about 0.00005 mm.

FIGS. 9 to 14 show the assembled prosthesis 2 in different relative positions.

Figures 9, 9A:
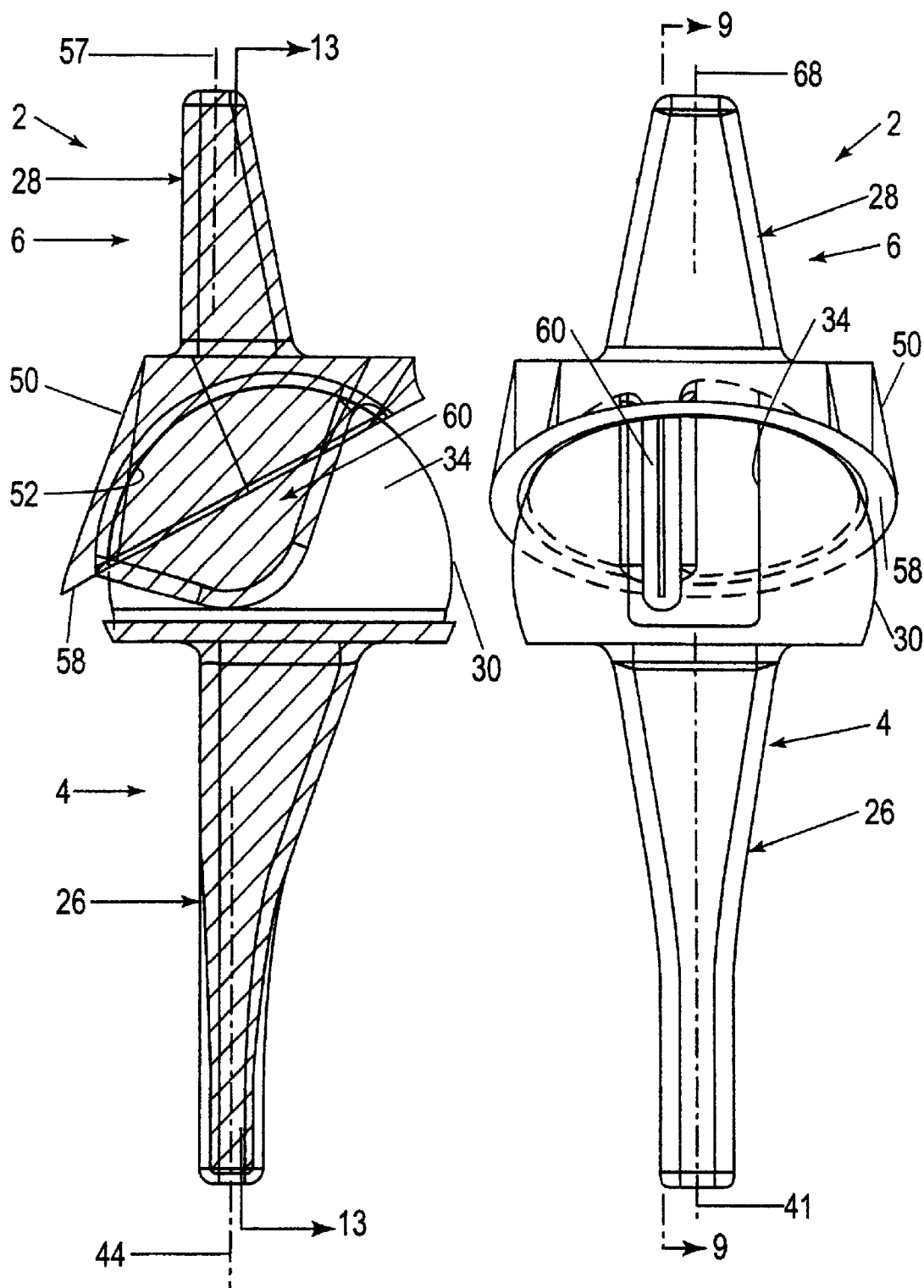
FIG. 9 is a cross-sectional side view of an assembled prosthesis in a neutral position.
FIG. 9A is a cross-sectional underside plan view of an assembled prosthesis in a neutral position.
Figure 10:
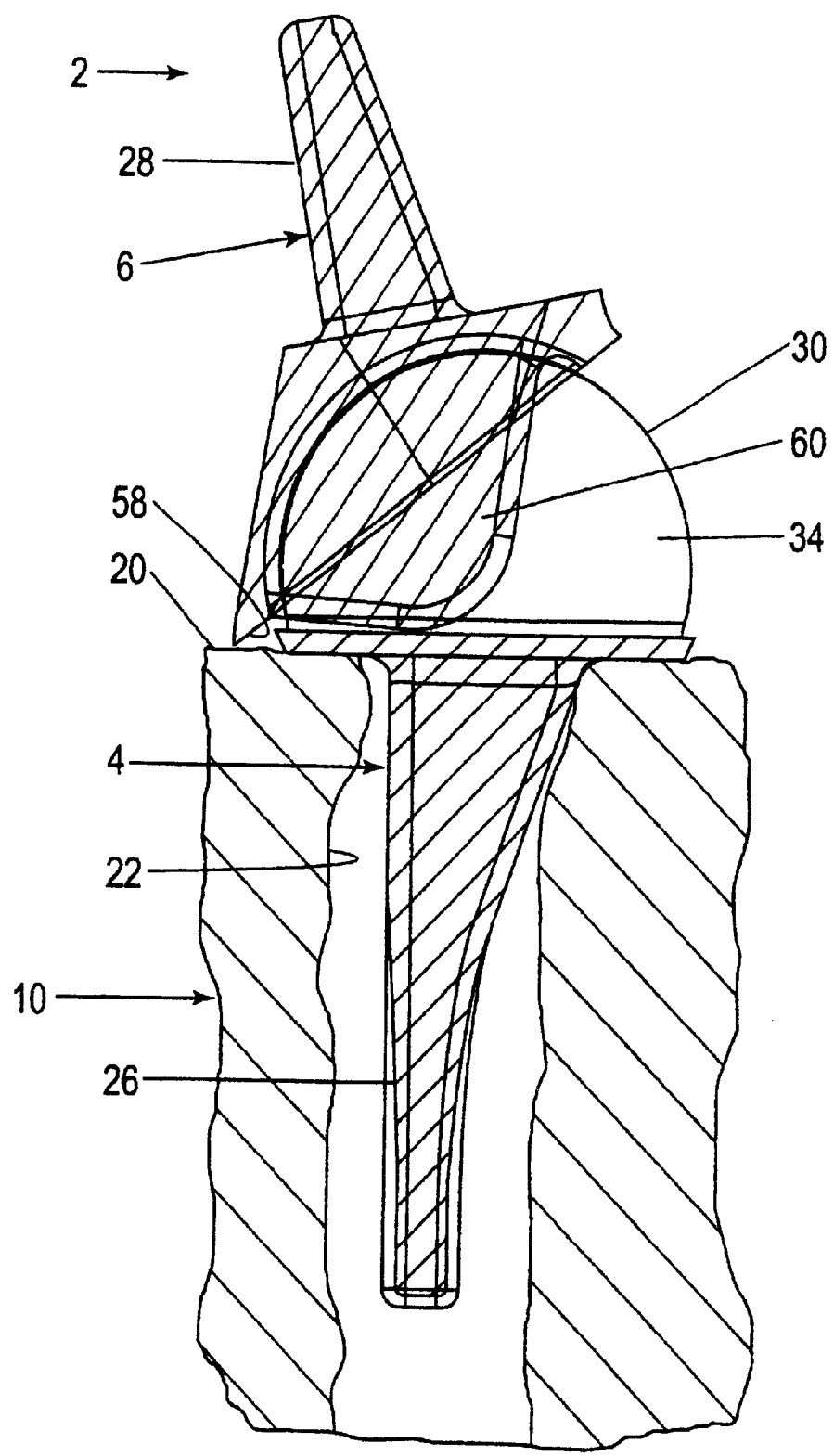
FIG. 10 is a schematic cross-sectional side view of an assembled prosthesis with 10° extension.
Figure 12:
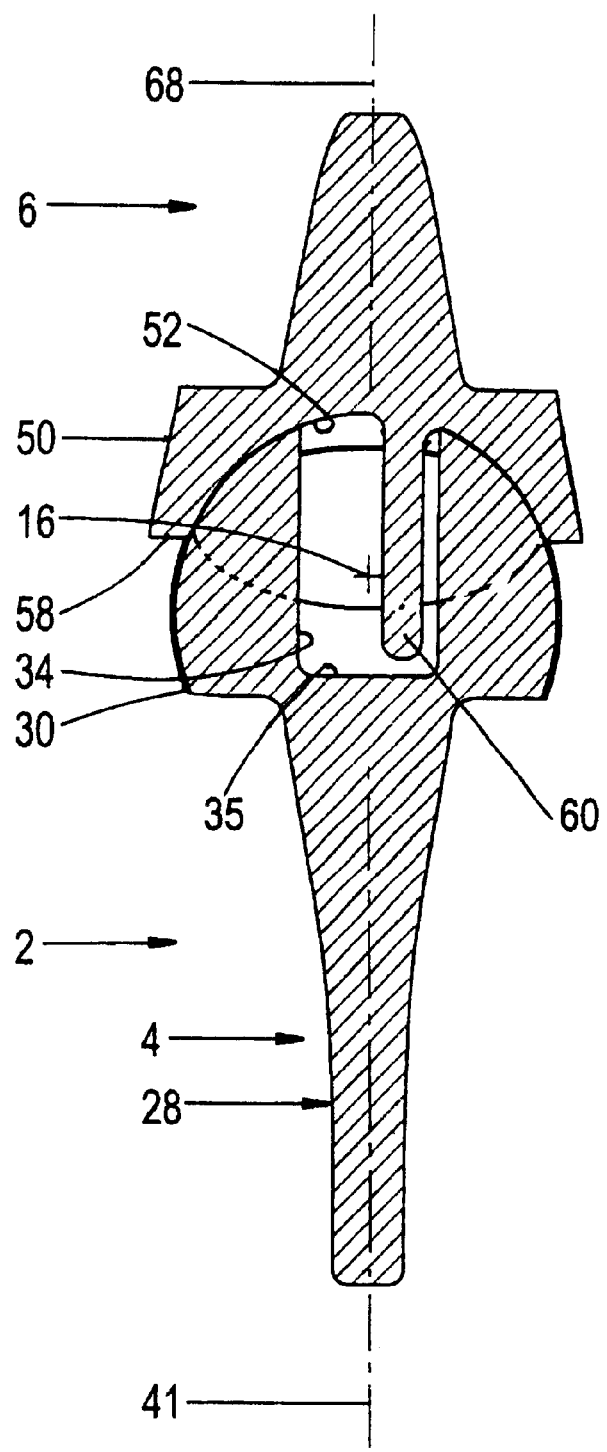
FIG. 12 is a schematic plan view of the assembled prosthesis.

As best seen in FIGS. 10 and 12, in the assembled joint, the ball 30 is located partly within the body 50 of the socket component 6 so that the spherical surface 30 engages the concave spherical surface 52. The peg 60 is located within the slot 34. As can be seen, the peg 60 is a loose fit within the slot 34. This permits biaxial rotation about the axes 14 and 16. The peg is not interlocked in the socket because the peg has planar side faces 61 and 63 which are normally spaced from the planar sidewalls 37 and 39 of the slot 34. Generally speaking the tendons of the finger holds the components of the prosthesis together. FIGS. 9 and 9A show the prosthesis 2 in a neutral position. As shown in plan in FIG. 9A, the central planes 41 and 68 are coplanar and the centrelines 44 and 57 are parallel but offset relative to one another by a distance of $L_2$ minus $L_3$, as is apparent from FIG. 9. The curved central portion 64 of the peg 60 is located just above the base surface 35 of the slot 34, as shown in the neutral position in the section view of FIG. 12. In the same view, it will be appreciated that the peg 60 is located in an offset position in the slot 34, by the distance $L_1$ relative to the central planes 41 and 68.

FIG. 10 shows the socket component 6 rotated through about 10° so as to provide about 10° of digital extension. This is limited by the dorsal side of the lip 58 engaging the metacarpal end face 20.

Figure 11:
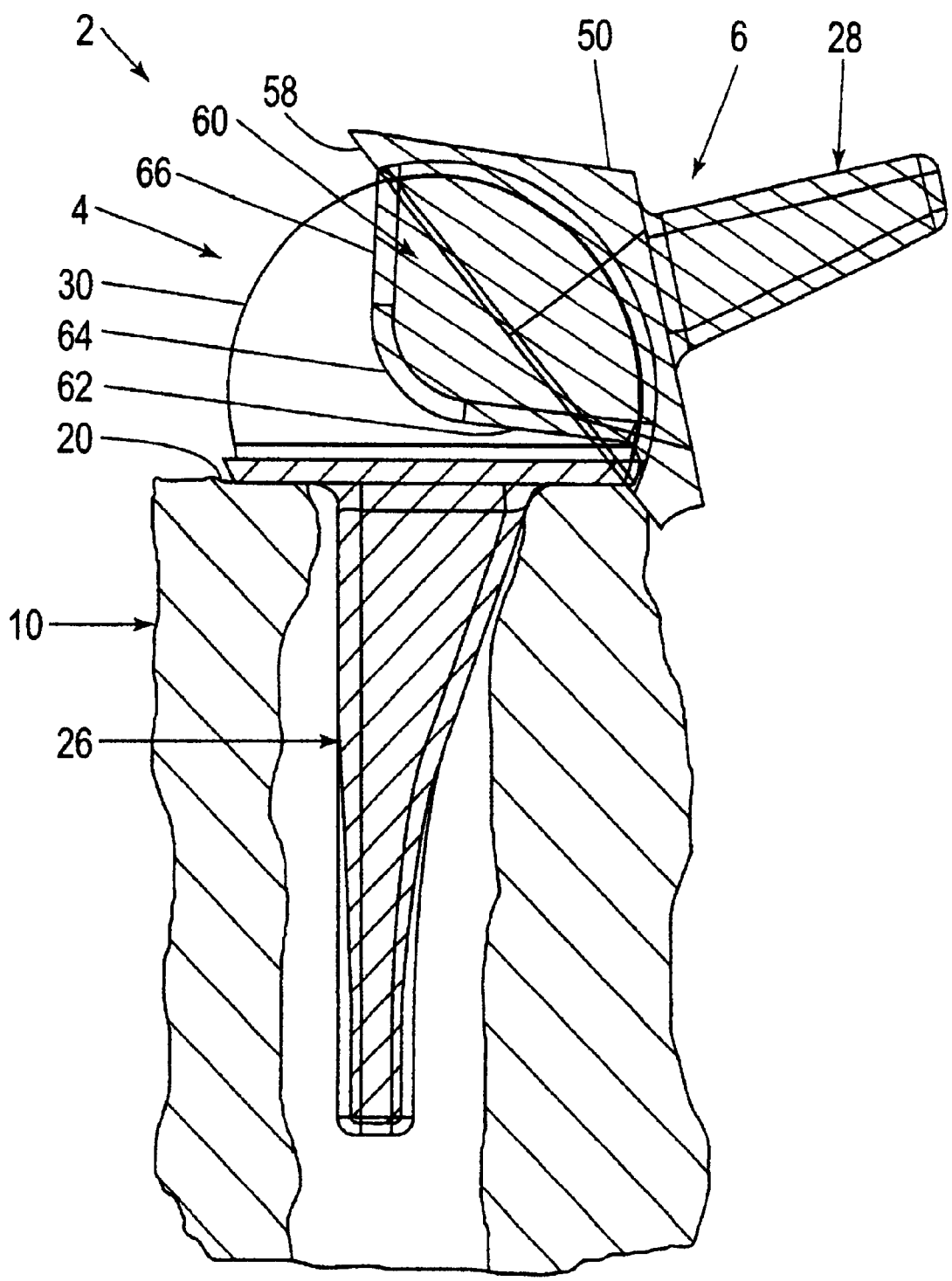
FIG. 11 is a schematic cross-sectional side view of an assembled prosthesis with 80° flexion.

FIG. 11 shows the socket component 6 rotated about 80° in the opposite direction from the neutral position so as to provide a useful range of flexion. Flexion is, generally speaking, limited by the volar edge portion 62 of the peg engaging the base surface 35 of the slot 34 or by the volar side of the lip 58 engaging the metacarpal end face 20.

FIG. 12 is a plan view (from the dorsal side) of the prosthesis in the neutral position in which the central planes 41 and 68 are coplanar.

Figure 13:
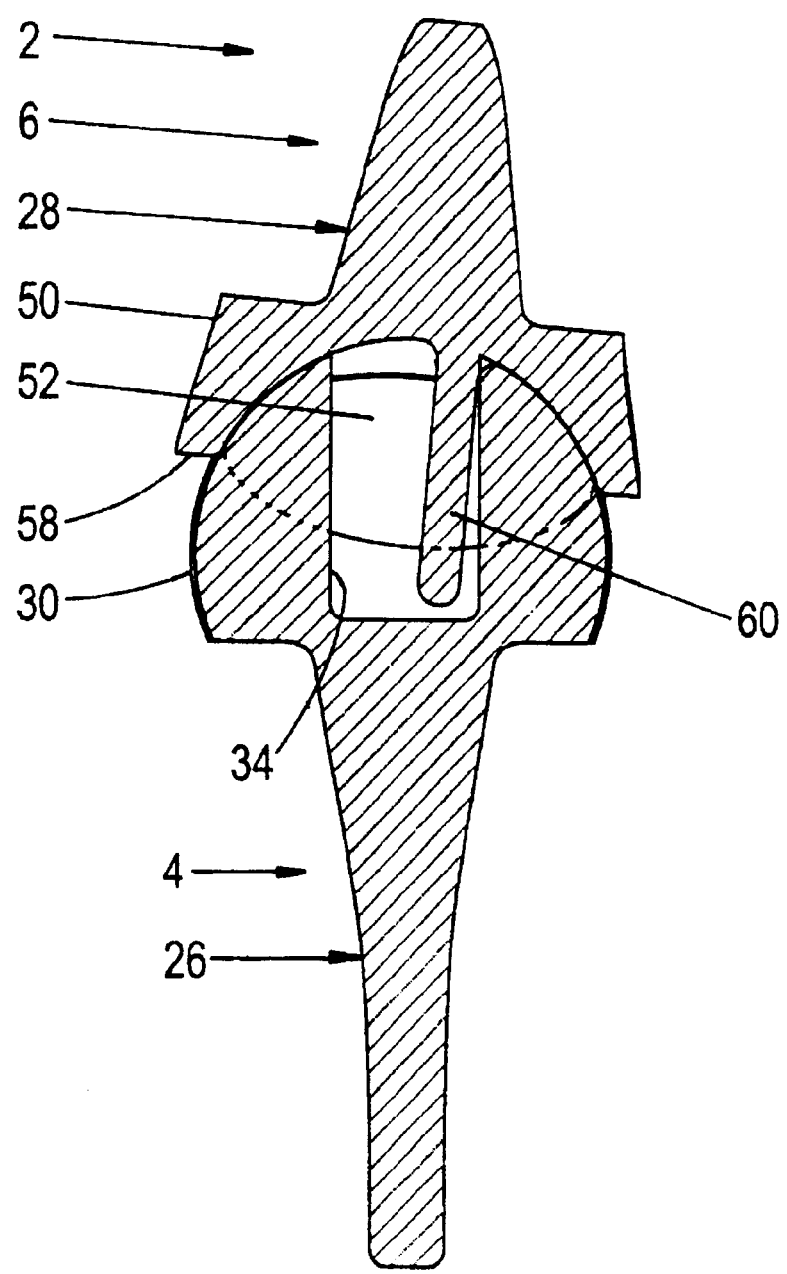
FIG. 13 is a schematic plan view of the prosthesis with 5° ulnar deviation.

FIG. 13 is a schematic cross-sectional plan view in which the socket component 6 is rotated through about 5° of rotation about the (vertical) axis 16 which provides about 5° of ulnar deviation. The amount of ulnar deviation is limited by the base of the peg 60 engaging the top edge of the slot 34, as shown in FIG. 13.

Figure 14:
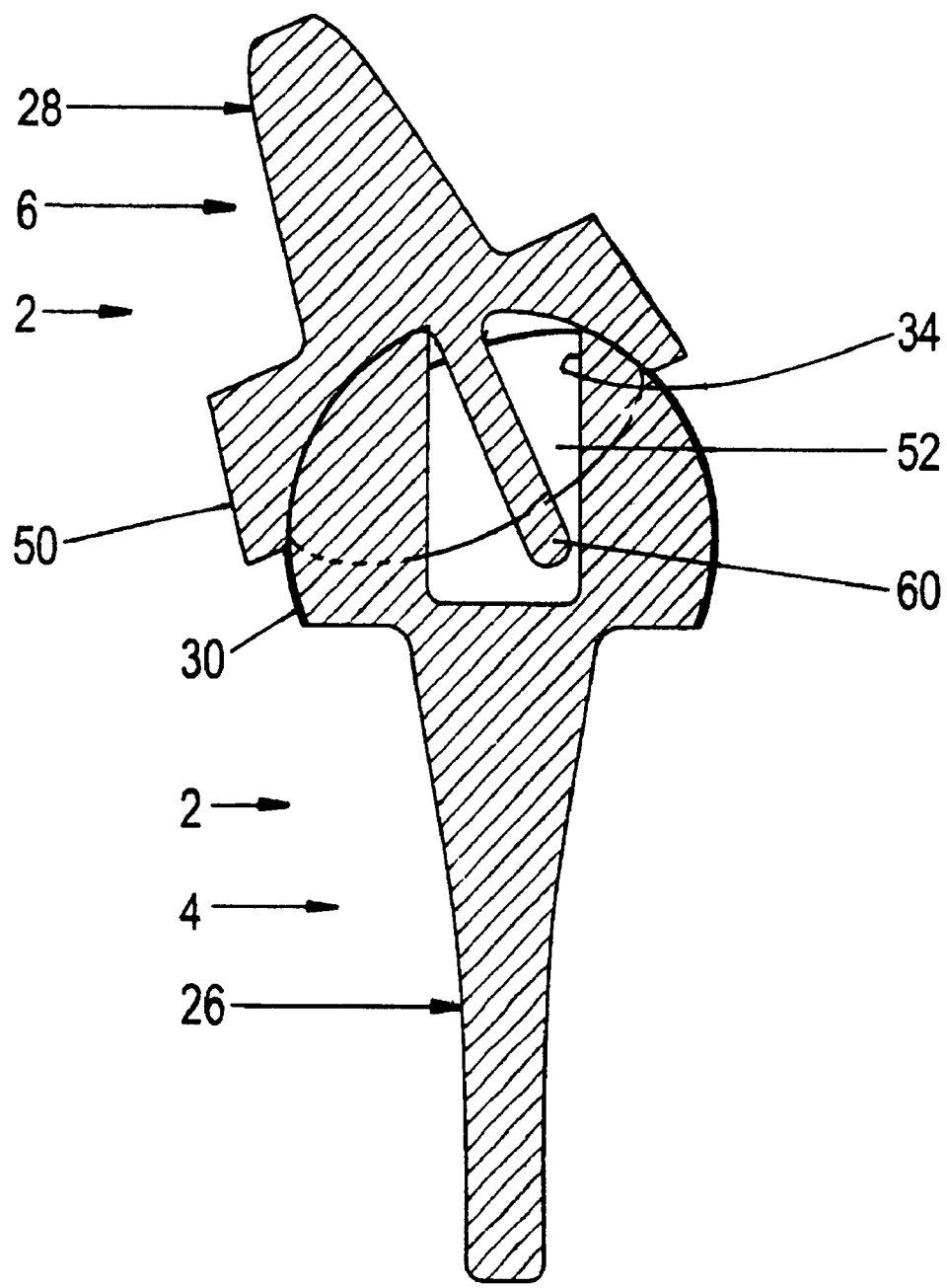
FIG. 14 is a schematic plan view of the prosthesis with 25° radial deviation.

FIG. 14 is a similar view to FIG. 13 but shows the socket component 16 rotated through about 25° in the opposite direction so as to provide about 25° of radial deviation. Because of the offset of the peg 60 in the slot 34, a greater degree of radial deviation is made possible. The extent of radial deviation is limited by the base of the peg 60 coming into engagement with the opposite upper periphery of the slot 34.

As indicated above, the components 4 and 6 of the invention can be made in a range of different sizes. These are set out in the Table below (all measurements in mm).

| Size | $R^1$ | Length of stem 26 | Length of stem 28 | Total joint length |
|---|---|---|---|---|
| Extra small | 4.50 | 14.8 | 7.5 | 29.05 |
| Small | 5.45 | 16.7 | 8.3 | 33.14 |
| Medium | 6.40 | 18.5 | 9.3 | 37.64 |
| Large | 7.30 | 21.4 | 10.5 | 42.83 |
| Extra Large | 8.25 | 23.5 | 11.5 | 47.43 |

This invention possesses a number of advantageous characteristics. First, it is relatively simple and robust to construct, there is no need for interlocking of the two components together. It will be noted that peg 60 is a loose fit in the slot 34. There is no need for any undercutting or other interlocking members associated with the peg and/or slot 34. This simplifies manufacture and assembly. The lip 58 also tends to prevent volar subluxation of the joint. More particularly, the dorsal side of the lip 58 contributes to the stability of the joint because it will normally engage the ball surface 30 so as to prevent volar subluxation. Also the base surfaces 32 and 54 prevent prosthesis subsidence into the canals 22 and 27 respectively. Further, the mounting stems 26 and 28 are relatively easily fixed to the bone by the use of known cements. Thus, in the final prosthesis, the joint is semi-constrained providing stability against recurring ulnar and volar forces but still allowing a functional range of flexion and ulnar and radial deviation and a small amount of axial rotation.

What is claimed is:

1. A prosthesis (2) for replacing a joint between first and second articulating bones (10,12) the prosthesis comprising first and second joint members (4,6) and wherein:
    the first joint member includes a first mounting member (26) which in use is mounted in an intramedullary canal (22) of the first bone;
    the second joint member includes a second mounting member (28) which in use is mounted in an intramedullary canal (27) of the second bone;
    the first joint member has a ball (30) having a first part spherical surface and a slot (34) extending transversely through the ball, the slot having a slot base (35) which extends diametrically across the ball;
    the second joint member has a socket (52) having a second part spherical surface which is complementary to first spherical surface and a guide peg (60) which projects from the second spherical surface and in use is located in said slot; and
    wherein the guide peg is loose fit within the slot thereby permitting biaxial rotation of the second member relative to the first member about at least first and second axes (14,16).

2. A prosthesis according to claim 1 wherein the slot has first and second parallel sidewalls (37,39) which are perpendicular to the slot base (35) having a slot central plane (41) midway therebetween.

3. A prosthesis according to claim 2 wherein the guide peg has first and second parallel side faces (61, 63) having a peg central plane (65) midway therebetween.

4. A prosthesis according to claim 3 wherein the prosthesis has a neutral position in which the first and second mounting members are generally aligned wherein the peg central plane (65) is offset relative to the slot central plane (41) by a first predetermined distance ($L_1$).

5. A prosthesis according to claim 4 wherein said first predetermined distance ($L_1$) is in the range 0.163 $R_1$ to 0.181 $R_1$ and most preferably 0.172 $R_1$, where $R_1$ is the radius of said first part spherical surface.

6. A prosthesis according to claim 4 wherein third and fourth limits of rotation of the second member relative to the first member about said second axis are defined by first and second side faces (61,63) of the peg engaging the first and second sidewalls (37,39) of the slot respectively.

7. A prosthesis according to claim 6 wherein the ball has a base face (32) which lies in a ball base plane which is normal to a centreline (44) of the first mounting member and wherein the centre (33) of said first spherical surface is offset relative to the centreline of the first mounting member by a third predetermined distance ($L_3$).

8. A prosthesis according to claim 7 wherein said third predetermined distance ($L_3$) is in the range 0.18 $R_1$ to 0.26 $R_1$, where $R_1$ is the radius of said first part spherical surface.

9. A prosthesis according to claim 7 wherein the free edge of guide peg is rounded, as seen in cross-section transversely through the side peg.

10. A prosthesis according to claim 9 wherein the first and second sidewalls meet the slot base at rounded corner portions (70).

11. A prosthesis according to claim 1 wherein the guide peg has a free edge (62,64,66) which projects from said socket and wherein the said free edge does not contact said slot base (35) except a first limit of rotation about said first axis.

12. A prosthesis according to claim 11 wherein said free edge includes first and second relatively straight portions (62, 66) with a curved portion (64) therebetween and wherein said first straight portion engages the slot base to define said first limit of rotation.

13. A prosthesis according to claim 11 wherein the socket is encircled by an annular lip (58).

14. A prosthesis according to claim 13 wherein the lip lies in a lip plane which is inclined relative to a centreline (57) of the second mounting member.

15. A prosthesis according to claim 14 wherein the socket is formed in a body (50) which includes a base face (54) which lies in a base plane which is normal to the centreline (57) of the second mounting member and wherein said lip plane is located at an acute (B) angle relative to said base plate.

16. A prosthesis according to claim 15 wherein said acute angle is in the range 25° to 35° and most preferably 28°.

17. A prosthesis according to claim 15 wherein said second spherical surface has a center (59) which is offset relative to the centerline of the second mounting member by a second ($L_2$).

18. A prosthesis according to claim 17 wherein the second predetermined distance ($L_2$) is in the range 0.36 $R_1$ to 0.44 $R_1$ and most preferably 0.4 $R_1$, where $R_1$ is the radius of said first part spherical surface.

19. A prosthesis according to claim 18 wherein the thickness of the peg is in the range 0.19 $R_1$ to 0.21 $R_1$ and most preferably 0.2 $R_1$, where $R_1$ is the radius of said first part spherical surface.

20. A prosthesis according to claim 18 wherein the width (W) of the slot is in the range 0.67 $R_1$ and 0.75 $R_1$, and most preferably 0.71 $R_1$ where $R_1$ is the radius of the first spherical surface.

21. A prosthesis according to claim 20 wherein the depth (D) of the slot is in the range 1.17 $R_1$ and 1.43$R_1$ and most preferably 1.3 $R_1$, is the radius of said first part spherical surface.

22. A prosthesis according to claim 13 wherein a second limit of rotation about said first axis is defined by the lip engaging, in use, part of said second bone.

23. A prosthesis according to claim 1 wherein the first and second mounting members comprise tapered stems.

24. A method of providing a prosthesis for a joint between first and second articulating bones (10,12) using a prosthesis (2) as defined in claim 1 which comprises removing adjacent parts of the first and second bones (10,12) to expose first and second intramedullary canals (22,27) and fixing the first and second mounting members (4,6) in the first and second intramedullary canals respectively.

25. The method of claim 24 wherein the first bone is a metacarpal bone (10) and the second bone is a phalangeal bone (12).

26. The method of claim 25 wherein the peg is offset in the socket in the ulnar direction when viewed from the dorsal side.

27. The method of claim 25 wherein the prosthesis provides about 90° flexion.

28. The method of claim 25 wherein the prosthesis provides about 10° extension.

29. The method of claim 25 wherein the prosthesis provides about 25° radial deviation.

30. The method of claim 25 wherein the prosthesis provides about 5° of ulnar deviation.

31. A method of manufacturing the prosthesis of claim 1 which comprises finishing said first and second spherical surfaces so as to have a high degree of sphericity.

32. The method of claim 31 wherein said sphericity is accurate to about 0.005 mm.

33. The method of claim 32 wherein surface finishes for the socket and guide peg have a tolerance of about 0.00005 mm.

\* \* \* \* \*

UNITED STATES PATENT AND TRADEMARK OFFICE
CERTIFICATE OF CORRECTION

PATENT NO. : 6,682,565 B1
DATED : January 27, 2004
INVENTOR(S) : Jeganath Krishnan It is certified that error appears in the above-identified patent and that said Letters Patent is hereby corrected as shown below:

Title page,
Item [75], Inventor, delete "Unley Park" and replace with -- Glen Osmond --.

Column 9,
Line 4, insert -- predetermined distance -- after "a second".
Line 19, insert -- where $R_1$ -- after "preferably 1.3 $R_1$".

Signed and Sealed this

Twenty-second Day of June, 2004

JON W. DUDAS
*Acting Director of the United States Patent and Trademark Office*